(12) United States Patent
Li et al.

(10) Patent No.: US 12,292,390 B2
(45) Date of Patent: *May 6, 2025

(54) SYSTEMS AND METHODS FOR OPERATING NON-DESTRUCTIVE TESTING DEVICES

(71) Applicant: Baker Hughes Holdings LLC, Houston, TX (US)

(72) Inventors: Yan Li, Winchester, NY (US); Kevin Andrew Coombs, Syracuse, NY (US)

(73) Assignee: Baker Hughes Holdings LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/588,300

(22) Filed: Feb. 27, 2024

(65) Prior Publication Data

US 2024/0192146 A1    Jun. 13, 2024

Related U.S. Application Data

(63) Continuation of application No. 17/245,846, filed on Apr. 30, 2021, now Pat. No. 11,927,546.

(51) Int. Cl.
*G01N 21/954* (2006.01)
*G02B 23/24* (2006.01)
*H04N 23/50* (2023.01)
*H04N 23/56* (2023.01)
*H04N 23/63* (2023.01)

(52) U.S. Cl.
CPC ....... *G01N 21/954* (2013.01); *G02B 23/2484* (2013.01); *H04N 23/56* (2023.01); *H04N 23/63* (2023.01); *H04N 23/555* (2023.01)

(58) Field of Classification Search
CPC .. G01N 21/954; G02B 23/2484; H04N 23/56; H04N 23/63; H04N 23/555; A61B 1/00097; A61B 1/005; A61B 1/00011
See application file for complete search history.

(56) References Cited

U.S. PATENT DOCUMENTS

| | | | |
|---|---|---|---|
| 7,679,396 B1* | 3/2010 | Kao | H03K 19/0948 326/27 |
| 2019/0268508 A1* | 8/2019 | Ono | H04N 25/78 |
| 2020/0178779 A1* | 6/2020 | Komoro | A61B 1/05 |

* cited by examiner

*Primary Examiner* — Nasim N Nirjhar
(74) *Attorney, Agent, or Firm* — Mintz, Levin, Cohn, Ferris, Glovsky and Popeo, P.C.

(57) ABSTRACT

Various systems and methods for non-destructive testing (NDT) devices are provided including a tubular housing including a proximal end and a distal end, a head section arranged at the distal end and a bendable articulation section secured to the head section. The NDT also includes a sensor within the head section configured to transmit a data set comprising a first signal to a first output terminal of the sensor and a second signal to a second output terminal of the sensor, wherein the first signal and the second signal are complementary differential signals and a first output signal cable coupled to the first output terminal and extending to a control unit arranged at the proximal end of the tubular housing. The first output signal cable is configured to transmit the first signal to the control unit and the second output terminal is terminated at a ground within the head section.

17 Claims, 4 Drawing Sheets

SYSTEMS AND METHODS FOR OPERATING NON-DESTRUCTIVE TESTING DEVICES

RELATED APPLICATION

This application is a continuation of U.S. patent application Ser. No. 17/245,846 filed on Apr. 30, 2021, the entire disclosure of which is incorporated herein by reference.

FIELD

The present application relates to non-destructive testing devices and methods utilizing differential signaling.

BACKGROUND

Certain equipment and facilities, such as power generation equipment and facilities, oil and gas equipment and facilities, aircraft equipment and facilities, manufacturing equipment and facilities, and the like, include interrelated systems and processes. For example, power generation plants can include turbine systems and processes for operating and maintaining the turbine systems. Likewise, oil and gas operations can include carbonaceous fuel retrieval systems and processing equipment interconnected via pipelines. Similarly, aircraft systems can include airplanes and maintenance hangars useful in maintaining airworthiness and providing for maintenance support. During equipment operations, the equipment can degrade, encounter undesired conditions such as corrosion, wear and tear, etc., potentially affecting overall equipment effectiveness. Certain inspection techniques, such as non-destructive inspection techniques or non-destructive testing (NDT) techniques, can be used to detect undesired equipment conditions.

SUMMARY

In general, systems and methods are provided for controlling non-destructive testing devices.

In one embodiment, a NDT device is provided having a tubular housing including a proximal end and a distal end. The tubular housing can include a head section arranged at the distal end, and a bendable articulation section secured to the head section and arranged proximal to the head section. A sensor can be arranged within the head section, and include a first output terminal having an output signal cable extending along the tubular housing to a control unit arranged at the proximal end of the tubular housing, and a second output terminal grounded within the tubular housing.

The sensor can have various configurations. For example, the sensor can be an optical sensor. In some implementations, the optical sensor can be configured to transmit a portion of a collected data set to the control unit via differential signaling through the first signal cable.

The first and second signal cables can have various configurations. For example, a first capacitor can be arranged in series with the first output terminal between the sensor and the control unit. In some implementations, a second capacitor can be arranged in series with the second output terminal between the sensor and the ground. In at least some implementations, the second output terminal can be grounded to at least one of an insulation shield of the tubular housing.

The NDT device can have various configurations. For example, the NDT device can include a pair of power cables extending along the tubular housing from the sensor to a power source arranged at the proximal end of the tubular housing. In some implementations, the NDT device can include an optical bundle extending along the tubular housing from the head section to a light source arranged at the proximal end of the tubular housing.

In another embodiment, a circuit is provided and includes a sensor configured to collect a data set. The sensor can include a first output terminal configured to transmit a first portion of the data set via differential signaling, and a second output terminal configured to transmit a second portion of the data set via differential signaling. The first portion and the second portion can be complementary differential signals. A control unit can be communicatively connected to an output signal cable connected to the first output terminal, and configured to receive the first portion of the data set from the output signal cable, whereas the second output terminal connects to a ground.

The first and second output terminals can have various configurations. For example, a first capacitor can be arranged in series with the output signal cable between the sensor and the control unit. In some implementations, a resistor connected to ground can be configured to communicatively couple to the output signal cable between the first capacitor and the control unit. In at least some implementations, a second capacitor can be arranged in series with the second output terminal between the sensor and the ground.

The sensor can have various configurations. For example, the sensor can be an optical sensor and the data set can be digitized image data. In some implementations, the control unit can be configured to process the first portion of the data set to produce an image.

In another embodiment, a circuit is provided and includes a sensor configured to collect a data set. The sensor can include a first output terminal configured to transmit a first portion of the data set via differential signaling, and a second output terminal configured to transmit a second portion of the data set via differential signaling. The first portion and the second portion can be complementary differential signals. A buffer chip can be configured to drive the first portion and second portion of the differential signal at a higher voltage. The buffer chip can include a first input terminal configured to connect with the first output port, a second input terminal configured to connect with the second output port, a first signal cable configured to transmit the driven first portion of the data set, and a second signal cable configured to transmit the driven second portion of the data set. A control unit can be communicatively coupled to the first output terminal and configured to receive the driven first portion of the data set from the first output terminal, whereas the second output terminal connects to a ground.

The first and second signal cables can have various configurations. For example, a first capacitor can be arranged in series with the first output terminal between the sensor and the control unit. In some implementations, a second capacitor can be arranged in series with the second output terminal between the sensor and the ground.

The sensor can have various configurations. For example, the sensor can be an optical sensor and the data set can be digitized image data. In some implementations, the control unit can be configured to process the first portion of the data set to produce an image. In at least some implementations, the sensor and buffer chip can be arranged within a distal head section of a tubular housing of a non-destructive testing device, and the control unit can be arranged at a proximal end of the tubular housing.

BRIEF DESCRIPTION OF THE DRAWINGS

These and other features will be more readily understood from the following detailed description taken in conjunction with the accompanying drawings, in which.

Figure 1:
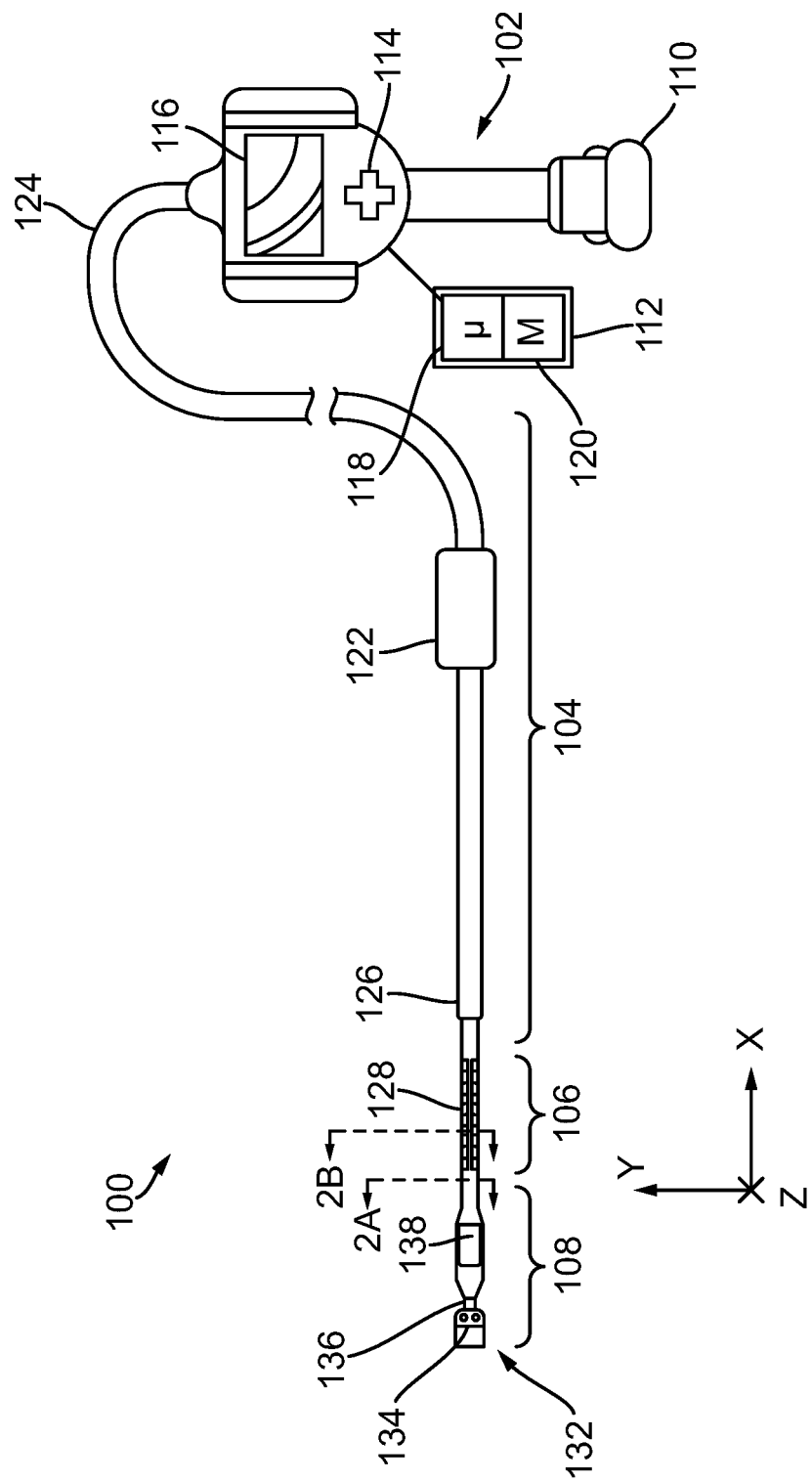
FIG. 1 is a schematic illustration of one exemplary embodiment of a non-destructive testing (NDT) device.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain exemplary implementations will now be described to provide an overall understanding of the principles of the structure, function, manufacture, and use of the devices and methods disclosed herein. One or more examples of these implementations are illustrated in the accompanying drawings. Those skilled in the art will understand that the devices and methods specifically described herein and illustrated in the accompanying drawings are non-limiting exemplary implementations and that the scope of the present invention is defined solely by the claims. The features illustrated or described in connection with one exemplary embodiment may be combined with the features of other implementations. Such modifications and variations are intended to be included within the scope of the present invention.

Certain NDT devices can be used to observe the inner mechanisms of complex machines, such as turbines and oil and gas equipment. NDT devices (e.g., borescopes, endoscopes, etc.) can be fed through these complex machines to perform maintenance checks with dismantling the whole machine. Such NDT devices require the ability to be actuated in order to maneuver through the small openings of these complex machines. Therefore, it is beneficial to increase the maneuverability and accuracy of an NDT device.

Various devices and methods are provided for using a NDT device to observe equipment. Non-destructive testing systems and devices can be used to inspect a variety of equipment and facilities without destroying the systems and/or devices being inspected. In certain exemplary implementations, the NDT systems and devices can include cameras and other measurement devices to obtain images and data of the equipment and facilities as well as inside the equipment and facilities. In use, the measurement devices and cameras that can be inserted into various locations in or around the equipment and facilities. The measurement devices and cameras can remotely couple to other devices that an operator can use to view the data gathered by the measurement device and camera as well as control the measurement device and camera. In some implementations, buttons, a joystick, and/or relative control gestures on a touchscreen associated with the NDT system or device, can be used to control a positioning of the imaging device in an asset (e.g., to move the imaging device from a first position to a second position). However, space within a tubular housing of an NDT device can be at a premium, and the more features an NDT device includes can negatively impact the flexibility of the NDT device due to the need of running cables down the length of the NDT device for each additional sensor. Due to this limitation, the removal of cables running down the tubular housing of an NDT device can increase its flexibility and maneuverability while keeping the same functions. This may avoid the deficiencies of the prior art techniques discussed above. By removing a cable for a sensor located in the head section of the NDT device, flexibility of the NDT can be increased, and along with increasing the available space within the tubular housing for additional sensors or lighting bundles. Some implementations disclosed herein can be advantageous as they can allow for the use of an optical sensor using differential signaling without the need of both portions of the differential signals being transmitted to a control unit to produce an image.

In order to actuate the NDT system, various positioning systems can be used which can bend a distal end of the NDT system to varying degrees of articulation. For example, a plurality of cables can extend along the length of the NDT system and be actuated by various motors arranged at a proximal end of the NDT system. Additionally, in order to illuminate a target area within assembled equipment or device, a light bundle can be arranged within the working channel of the NDT device. Additionally, an optical sensor, such as a camera can be arranged at the distal end of the NDT device in order to observe the internal mechanism of a device.

In order to transmit a signal from the optical sensor to a control unit, which can display the image collected by the optical sensor, differential signaling can be used. Differential signaling is a method for electrically transmitting information using two complementary signals, such as a positive signal and a negative signal. The technique sends the same electrical signal as a differential pair of signals, each in its own conductor. The pair of conductors can be wires or traces on a circuit board. The receiving circuit responds to the electrical difference between the two signals, rather than the difference between a single wire and ground. However, as described in detail below, differential signaling can be used where only one of a single signal of the pair of signals reaches a receiver. This technique is called single-ended signaling using differential signaling, and reduces the need for an additional signal cable running down the length of an NDT device.

Figure 4:
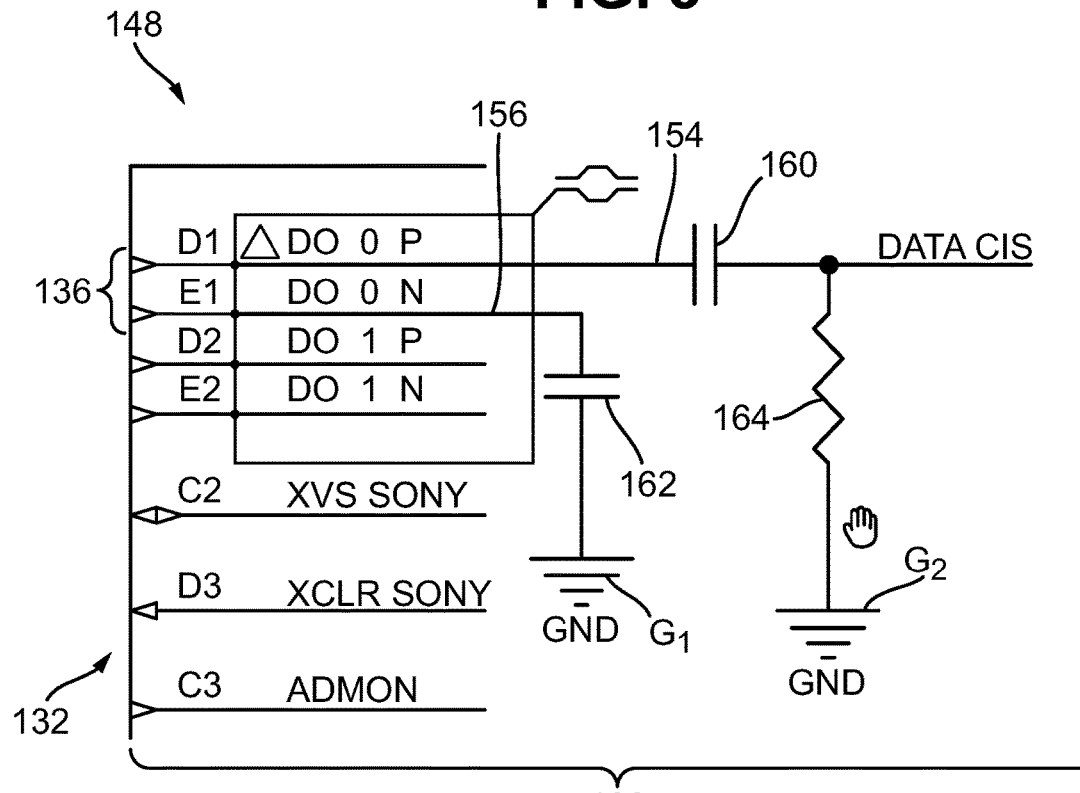
FIG. 4 is a schematic illustration of one exemplary embodiment of a differential signaling circuit diagram of an NDT device.
Figure 5:
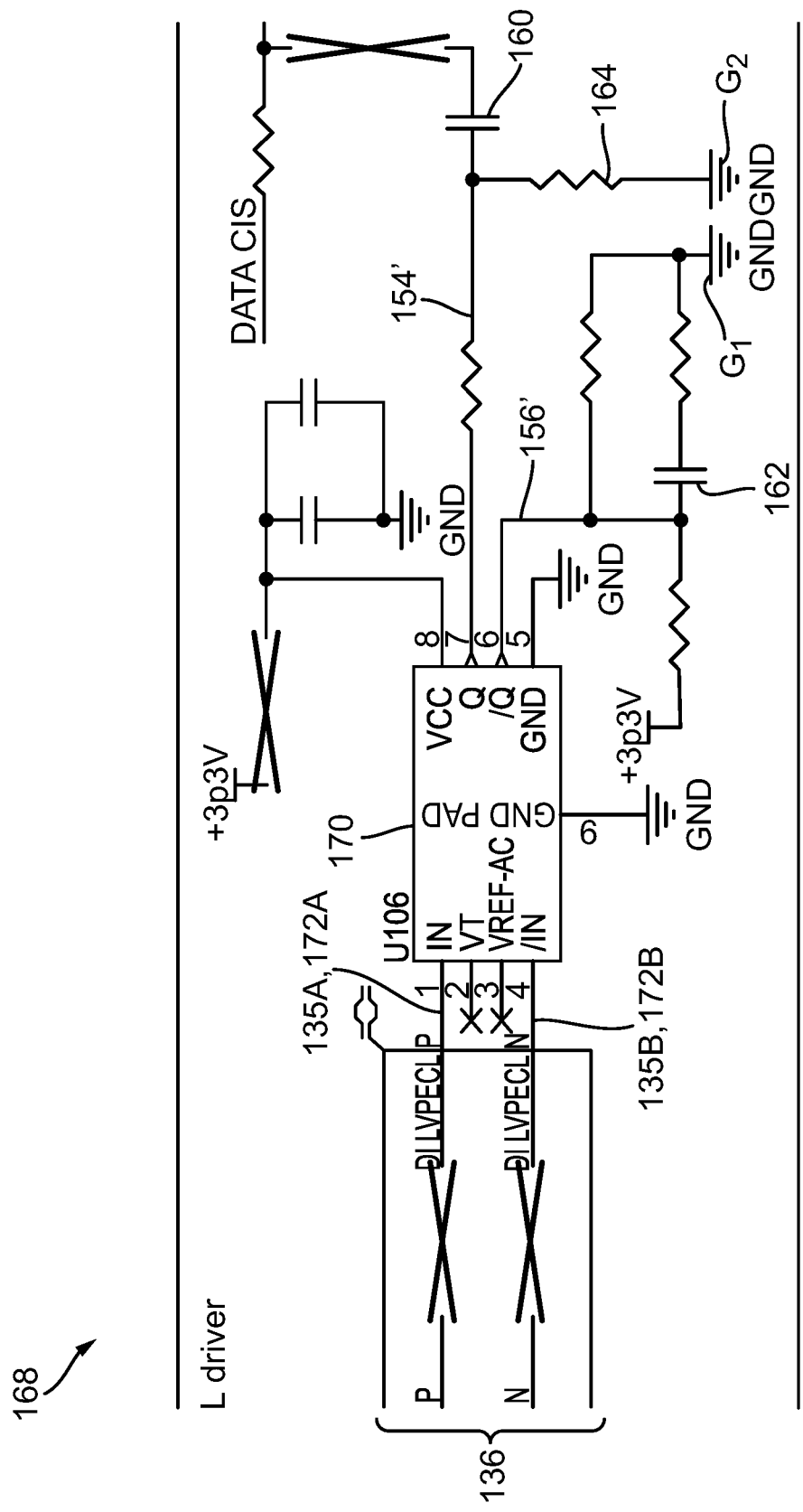
FIG. 5 is a schematic illustration of another exemplary embodiment of a differential signaling circuit diagram of an NDT device.

Various implementations of NDT systems are disclosed herein. In general, FIG. 1 illustrate one embodiment of a NDT device 100 having tubular housing including a head section and a bendable articulation section. FIG. 4 illustrates an embodiment of a differential signaling circuit diagram of an NDT device. FIG. 5 illustrates another embodiment of a differential signaling circuit diagram of an NDT device utilizing a buffer chip.

Referring now to FIG. 1, a schematic illustration of an NDT device 100 is generally depicted. The NDT device 100 includes a control unit 102, a conduit section 104, a bendable articulation section 106, and a head section 108. Each of the sections 104, 106, and 108 can be integral with one another, or can be removable (e.g., detachable) from each section depending on specific applications. For example, if a longer conduit section 104 is required, the shorter conduit section 104 can be removed and a longer conduit section 104 can be attached to the control unit 102. As depicted, the conduit section 104 is suitable for insertion into a variety of locations, such as inside turbomachinery, equipment, pipes, conduits, underwater locations, curves, bends, inside or outside of an aircraft system, and the like.

Referring still to FIG. 1, the control unit 102 includes a control unit housing 110, a controller 112, a directional input 114, and a screen 116. The controller 112 can include a processor 118 and a readable memory 120 containing computer readable instructions which can be executed by the processor 118 in order to actuate the NDT device 100 and control a variety of sensors within the head section 108. The controller 112 is communicatively connected to the control unit 102. In implementations, the controller 112 can be arranged within the control unit housing 110, or can be arranged outside the control unit housing 110. The directional input 114 is for a user to input direction controls to the control unit 102 in order to actuate the NDT device 100. The screen 116 can display visual information being received by an optical sensor arranged in the head section 108, which allows the user to better guide the NDT device 100 using the directional input 114. In implementations, the directional input 114 and the screen 116 are communicatively connected to the controller 112 via signal 121, which can be a hard-wired connection or a wireless signal, such as WI-FI™ or Bluetooth™.

Referring still to FIG. 1, the conduit section 104 includes a tubular housing 122 including a proximal end 124 and a distal end 126. In implementations, the control unit 102 is arranged at the proximal end 124 of the tubular housing 122, and the bendable articulation section 106 is arranged at the distal end of the tubular housing 122. The tubular housing 122 can be a flexible member along its whole length, or can be rigid at the proximal end 124 and become more flexible travelling down the length of the conduit section 104 towards the distal end 126. Additionally, in implementations, the tubular housing 122 can be formed from a non-porous material to prevent contaminants from entering the NDT device 100 via the conduit section 104.

Referring still to FIG. 1, the bendable articulation section 106 includes a bendable neck 128. The bendable neck 128 is arranged at the distal end 126 of the tubular housing 122, and is able to be actuated 360° in the Y-Z plane. The bendable neck 128 can be wrapped in a non-porous material to prevent contaminants from entering the NDT device 100 via the bendable articulation section 106.

Referring still to FIG. 1, the head section 108 includes a head assembly 132. The head assembly 132 includes one or more lights 134 (e.g., LEDs or a fiber optic bundle with lights at the proximal end), a camera 136, and one or more of a sensor 138. In general, the head section 108 includes one or more sensors that collect data about the surrounding environment (e.g., a sensor 138, a camera 136, etc.).

As mentioned above, the camera 136 of the NDT device 100 can provide images and video suitable for inspection to the screen 116 of the control unit 102. The lights 134 can be used to provide for illumination when the head section 108 is disposed in locations having low light or no light. The sensor 138 can record data including temperature data, distance data, clearance data (e.g., distance between a rotating element and a stationary element), flow data, and so on. In certain implementations, the NDT device 100 includes a plurality of replacement head assemblies 132. For example, the head assemblies 132 can include retrieval tips such as snares, magnetic tips, gripper tips, and the like. The head assemblies 132 can additionally include cleaning and obstruction removal tools, such as wire brushes, wire cutters, and the like. The head assemblies 132 can additionally include tips having differing optical characteristics, such as focal length, stereoscopic views, 3-dimensional (3D) phase views, shadow views, and so on. Additionally or alternatively, the head section 108 includes a removable and replaceable portion of the head section 108. Accordingly, a plurality of the head sections 108, bendable necks 128, and conduit sections 104 can be provided at a variety of diameters from approximately one millimeter to ten millimeters or more.

During use, the bendable articulation section 106 can be controlled, for example, by the control inputs (e.g., relative control gestures, physical manipulation device) from the directional input 114. The directional input can be a joystick, D-pad, touch pad, trackball, optical sensor, or a touchscreen over the screen 116. The directional input 114 can also be a similar device that is located outside the control unit housing 110 and connected by wire or wireless means. In particular, a set of control inputs can be used to control the bendable articulation section 106. The bendable articulation section 106 can steer or "bend" in various dimensions, and can use actuators and wires, or a combination thereof, arranged within the control unit 102, to adjust the orientation (e.g., a positioning) of the head section 108. The actuators can be electric, pneumatic, or ultrasonically operated motors or solenoids, shape alloy, electroactive polymers, dielectric elastomers, polymer muscle material, or other materials. For example, the bendable articulation section 106 can enable movement of the head section 108 in an X-Y plane, X-Z plane, and/or Y-Z plane. Indeed, the directional input 114 can be used to perform control actions suitable for disposing the head section 108 at a variety of angles. In this manner, the head section 108 can be positioned to visually inspect desired locations. Once the head section 108 is in a desired position, the camera 136 can operate to capture, for example, a stand-still visual image or a continuous visual image, which can be displayed on the screen 116 of the control unit 102, and can be recorded by the NDT device 100. In implementations, the screen 116 can be multi-touch touch screens using capacitance techniques, resistive techniques, infrared grid techniques, and the like, to detect the touch of a stylus and/or one or more human fingers. Additionally or alternatively, captured visual images can be transmitted into a separate storage device for later reference.

Figure 2A:
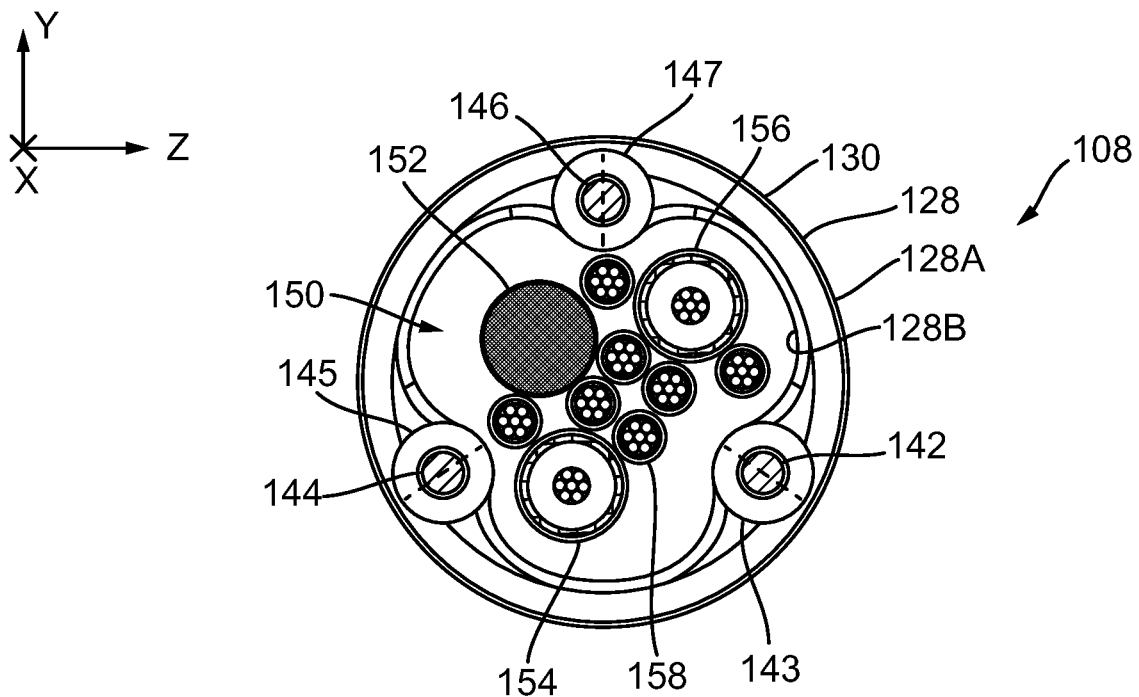
FIG. 2A is a cross-sectional schematic illustration of the NDT device of FIG. 1 taken along a head section.
Figure 2B:
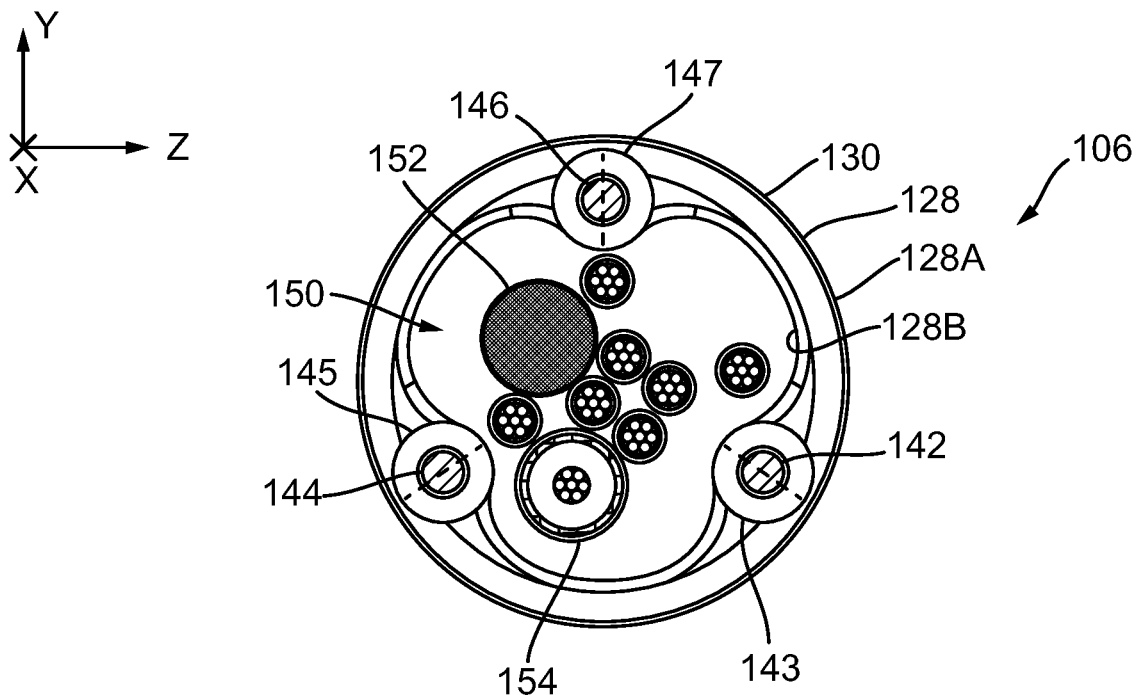
FIG. 2B is a cross-sectional schematic illustration of the NDT device of FIG. 1 taken along an articulation section.

Referring now to FIGS. 2A-2B, a cross-sectional schematic illustration of the head section 108 (as shown in FIG. 1) of the NDT device 100 taken generally along line 2A in FIG. 1 is depicted in FIG. 2A, and a cross-sectional schematic illustration of the articulation section 106 (as shown in FIG. 1) of the NDT device 100 taken generally along line 2B in FIG. 1 is depicted in FIG. 2B. As depicted, the control cables 142, 144, and 146 pass through sheaths 143, 145, and 147 along the length of the tubular housing 122. A working volume 150 is arranged within the inner wall 122B of the tubular housing 122. The outer wall 122A of the tubular housing 122 protects the internal components of the tubular housing 122. In implementations, various objects, such as optical fibers 152, output terminals 154, 156, and power cables 158, may also be arranged within the working volume 150 along the length of the tubular housing 122. The sheaths 143, 145, and 147 can prevent wear against the optical fibers 152, output terminal 154, 156, and power cables 158 as the control cables 142, 144, and 146 are actuated to bend the bendable neck 128. The working volume can extend the whole length of the bendable articulation section 106 and the conduit section 104 (as shown in FIG. 1) to allow tools and devices to pass through the bendable neck 128 and the tubular housing 122 from the proximal end 124 to the distal end 126, through the bendable articulation section 106, and through the head section 108.

In some implementations, the greater the available space within the working volume 150, the greater the flexibility of the bendable neck 128. The optical fibers 152, output terminals 154, 156, and power cables 158 each take up a portion of the available space within the working volume 150. In some implementations, the optical fibers 152 are a fiber optic bundle formed from various fiber optic cables, with the fiber optic cables being connected to a light source arranged at the proximal end of the tubular housing 122. As illustrated in FIG. 2A, the output terminals 154 and 156 can be connected to the optical sensor 136 in order to provide the complementary differential signals from the optical sensor 136 to the controller 112. In an exemplary embodiment, the output terminal/signal cable 154 can transmit the positive signal, and the output terminal 156 can transmit the negative signal. Additionally, in some implementations, the signal cable 154 can be coaxial cables, having an intermediate insulating layer between the two conducting layers.

The distal end of the tubular housing 122, such as the head section 108, does not actuate and can be sustainably rigid. The articulating section 106, arranged just proximal to the head section 108 can bend in order to angle the head section at various angles. In order to increase the flexibility of the articulation section 106, the removal of the output terminal 156 occurs prior to the output terminal 156 passing into the articulating section 106, as illustrated in FIG. 2B. With the output terminal 156 removed, there is now additional free volume located within the working volume 150 when comparing the working volume of the head section 108 to the working volume of the articulating section 106. With the additional free volume present in the articulating section 106, the optic fiber 152, signal cable 154 and power cables 158 have more space to shift during bending of the bending neck 128, allowing for a larger articulation angle to be achieved.

Figure 3:
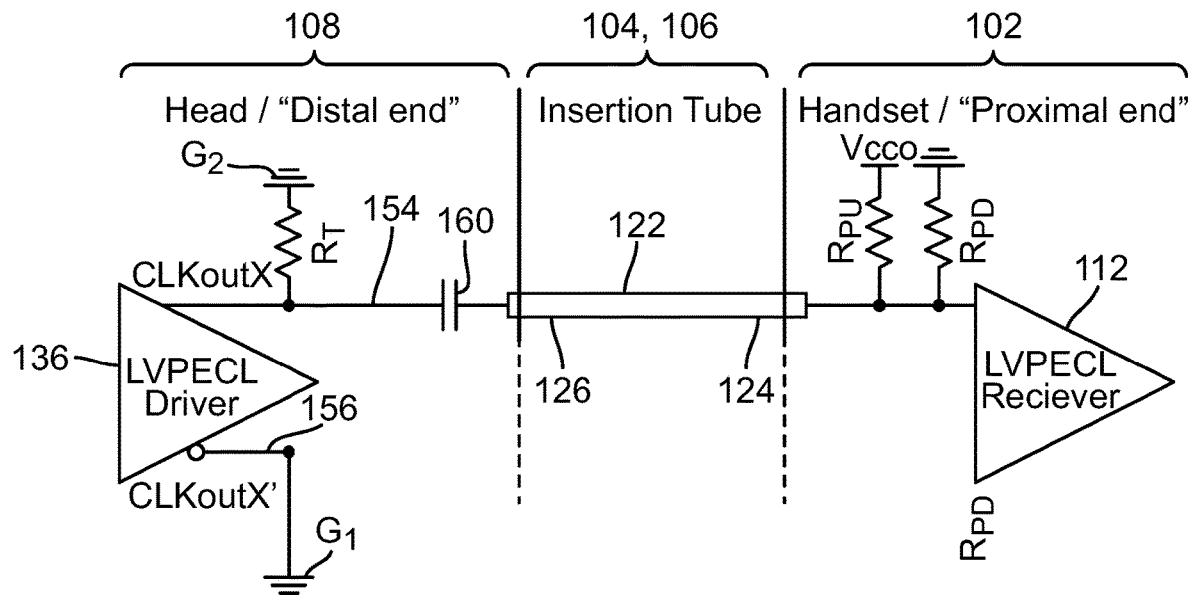
FIG. 3 is a schematic illustration of the circuit diagram of the NDT device of FIG. 1.

In order to operate the optical sensor 136 via differential, a signal is transmitted from the optical sensor 136 via the output terminals 154, 156. However, in order to increase the available free volume in the working volume, a signal cable connected to the output terminal 156 can be removed. As illustrated in FIGS. 3-4, the output terminal 156 is connected to a ground $G_1$ prior to extending past the head section 108. In some embodiment, the ground $G_1$ can be the insulating layer of a coaxial cable, or can be the tubular housing 122. As illustrated in FIG. 3, only the signal cable 154 passes from the head section 108, through the articulating section 106 and the conduit section 104, to the control unit 102, where the signal cable can be connected to the controller 112.

In order to display an image on the control unit 112, data needs to be transmitted from the optical sensor 136 to the controller 112. In some implementations, the optical sensor 136 transmits a data set including digitized data of an image via a positive differential signal along the signal cable 154. The digitized data can be interpreted by the controller 112 and displayed on the screen 116. An example frequency which the data set can be transmitted along the signal cable 154 can be 2.4 GHz, but any suitable signal can be used and should be appreciated by a person of ordinary skill.

An exemplary embodiment of a differential signaling circuit 148 is illustrated in FIG. 4. As depicted, the circuit 148 can include the optical sensor 136 and the output terminals 154, 156. In some implementations, prior to connecting with the ground $G_1$, the output terminal 156 can include a capacitor 162 arranged in series with the output terminal 156. Additionally, the signal cable 154 can includes a capacitor 160 arranged in series with the signal cable 154.

In an exemplary implementation, the capacitors 160, 162 can provide an AC coupling function, allowing a decoupling of DC voltages between a driver and a receiver. The capacitors 160, 162 can have a capacitance in the range of 1 pF-1 uF in order to provide the AC coupling function. Additionally, a resistor 164 can be connected to the signal cable 154 and coupled to a ground $G_2$. In an exemplary implementation, the resistor 164 provides a bias function (if connected to a power supply or ground). The resistor 164 can have a resistance of 500-500K ohms in order to provide the bias function. Additionally, if a resistor is inline with a signal, the resistor is arranged to provide signal integrity (damping). In some exemplary implementations, the resistor 164 can be arranged prior to the capacitor 160 along the signal cable 154. However, the resistor 164 can be arranged after to the capacitor 160 along the signal cable 154.

An exemplary embodiment of a differential signaling circuit 168 is illustrated in FIG. 5. As depicted, the circuit 168 can include the optical sensor 136 and the output terminals 154', 156', along with a buffer chip 170. The buffer chip 170 can drive the output signals from the optical sensor 136 at a higher voltage in order to transmit the data set along the output terminals 154', 156' a greater distance. In some implementations, the optical sensor includes output ports 135A, 135B, which can be configured to output the two complementary signals of a differential signal. Coupled to the output ports 135A, 135B are input ports 172A, 172B of the buffer chip 170. Similar to the circuit 148, prior to connecting with the ground $G_1$, the output terminal 156' can include a capacitor 162 arranged in series with the output terminal 156. Additionally, the signal cable 154' can includes a capacitor 160 arranged in series with the signal cable 154'. Additionally, a resistor 164 can be connected to the signal cable 154' and coupled to a ground $G_2$.

Certain exemplary implementations have been described to provide an overall understanding of the principles of the structure, function, manufacture, and use of the systems, devices, and methods disclosed herein. One or more examples of these implementations have been illustrated in the accompanying drawings. Those skilled in the art will understand that the systems, devices, and methods specifically described herein and illustrated in the accompanying drawings are non-limiting exemplary implementations and that the scope of the present invention is defined solely by the claims. The features illustrated or described in connection with one exemplary implementation may be combined with the features of other implementations. Such modifications and variations are intended to be included within the scope of the present invention. Further, in the present disclosure, like-named components of the implementations generally have similar features, and thus within a particular implementation each feature of each like-named component is not necessarily fully elaborated upon.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described implementations. Accordingly, the present application is not to be limited by what has been particularly shown and described, except as indicated by the appended claims. All publications and references cited herein are expressly incorporated by reference in their entirety.

The invention claimed is:

1. A non-destructive testing device, comprising:
a tubular housing including a proximal end and a distal end, the tubular housing including:
a head section arranged at the distal end;
a bendable articulation section secured to the head section and arranged proximal to the head section;
an optical sensor arranged within the head section, the optical sensor configured to transmit a data set comprising a first image signal to a first output terminal of the optical sensor and a second image signal to a second output terminal of the optical sensor, wherein the first image signal and the second image signal are complementary differential signals; and
a first output signal cable communicatively coupled to the first output terminal and extending along the tubular housing to a control unit having a processor and circuitry, arranged at the proximal end of the tubular housing, wherein the first output signal cable is configured to transmit the first signal from the sensor to the control unit,
wherein the second output terminal is terminated at a ground within the head section.

2. The circuit of claim 1, wherein the control unit is configured to process the first image signal to produce an image.

3. The non-destructive testing device of claim 1, wherein a first capacitor is arranged in series with the first output signal cable between the optical sensor and the control unit.

4. The non-destructive testing device of claim 1, wherein a second capacitor is arranged between the second output terminal and the ground.

5. The non-destructive testing device of claim 4, wherein the second output terminal is grounded to an insulation shield of the tubular housing.

6. The non-destructive testing device of claim 1, further comprising a pair of power cables extending along the tubular housing from the optical sensor to a power source arranged at the proximal end of the tubular housing.

7. The non-destructive testing device of claim 1, further comprising a second output signal cable communicatively coupled to the second output terminal, wherein the first output signal cable and the second output signal cable are provided as a coaxial cable and the second output signal cable is configured to be grounded to an insulating layer of the coaxial cable.

8. The non-destructive testing device of claim 1, further comprising an optical bundle extending along the tubular housing from the head section to a light source arranged at the proximal end of the tubular housing.

9. The non-destructive testing device of claim 1, further comprising:
a buffer chip provided between the sensor and the first output signal cable and configured to drive the first signal from the optical sensor to the control unit, the buffer chip comprising:
a first input terminal coupled to the first output terminal; and
a third output terminal coupled to the first output signal cable and configured to transmit the driven first signal from the optical sensor to the control unit.

10. A circuit, comprising
a sensor configured to collect an image data set, the sensor including:
a first output terminal configured to transmit a first representation of the image data set via differential signaling; and
a second output terminal configured to transmit a second representation of the image data set via differential signaling, wherein the first representation and the second representation are complementary differential signals; and
a control unit having a processor and circuitry, communicatively connected to the first output terminal by a first output signal cable connected to the first output terminal, and configured to receive the first representation of the image data set from the output signal cable,
wherein the second output terminal is terminated at a ground.

11. The circuit of claim 10, wherein a first capacitor is arranged in series with the first output terminal cable between the sensor and the control unit.

12. The circuit of claim 11, wherein a resistor connected to the ground is configured to communicatively couple to the output signal cable between the first capacitor and the control unit.

13. The circuit of claim 11, wherein a second capacitor is arranged in series with the second output terminal between the sensor and the ground.

14. The circuit of claim 10, wherein the sensor is an optical sensor and the image data set is digitized image data.

15. The circuit of claim 14, wherein the control unit is configured to process the first representation of the image data set to produce an image.

16. The circuit of claim 10, wherein the second output terminal is connected to a first end of a second output signal cable and wherein the first output signal cable and the second output signal cable are provided as a coaxial cable and a second end of the second output signal cable is grounded to an insulating layer of the coaxial cable.

17. The circuit of claim 14, wherein the sensor and the buffer chip are arranged within a distal head section of a tubular housing of a non-destructive testing device, and the control unit is arranged at a proximal end of the tubular housing.

* * * * *